United States Patent [19]

Wehling et al.

[11] 4,268,670

[45] May 19, 1981

[54] PROCESS FOR THE PREPARATION OF BENZIMIDAZOLYLBENZOFURANES

[75] Inventors: Bernhard Wehling, Cologne; Josef Bremen, Leverkusen, both of Fed. Rep. of Germany

[73] Assignee: Bayer Aktiengesellschaft, Leverkusen, Fed. Rep. of Germany

[21] Appl. No.: 113,933

[22] Filed: Jan. 21, 1980

[30] Foreign Application Priority Data

Feb. 8, 1979 [DE] Fed. Rep. of Germany ....... 2904829

[51] Int. Cl.$^3$ .................. C07D 405/04; C07D 405/14
[52] U.S. Cl. ..................... 542/435; 542/436; 548/255; 548/256; 548/261; 548/327; 548/330
[58] Field of Search ............... 548/327, 256; 542/435, 542/436

[56] References Cited

U.S. PATENT DOCUMENTS

| | | | |
|---|---|---|---|
| 3,864,333 | 2/1975 | Sahm et al. ............... | 260/346.22 X |
| 3,940,417 | 2/1976 | Schläepfer ................... | 548/327 |
| 4,143,055 | 3/1979 | Occelli ...................... | 260/346.22 X |
| 4,146,725 | 3/1979 | Meyer et al. ............... | 548/327 |

FOREIGN PATENT DOCUMENTS

2304265 1/1974 Fed. Rep. of Germany ...... 548/256

OTHER PUBLICATIONS

*Chemical Abstracts*, 72:90167y (1970) [Bordin, F., et al., *Gazz. Chim. Ital.* 1969, 99(11), 1177–1192].
Seemuth, P., et al., *J. Org. Chem.*, 43(15), 3063–3065 (1978).
Cagniant, P., et al., in *Advances in Heterocyclic Chemistry*, vol. 18 (Katritzky et al.–Editors), Academic Press, N.Y., 1975, p. 434.
Brooke, G., et al., *J. Chem. Soc.* (c), 580–584 (1968).

*Primary Examiner*—Richard A. Schwartz

*Attorney, Agent, or Firm*—Sprung, Felfe, Horn, Lynch & Kramer

[57] ABSTRACT

Optical brighteners of the formula

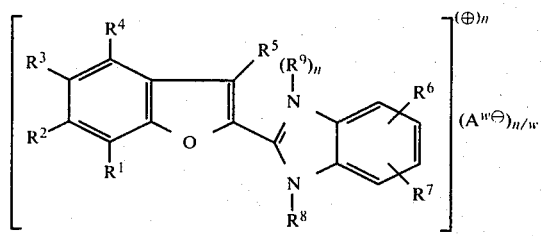

wherein
the radicals $R_1$ to $R_9$ are substituents customary in brightener chemistry,
$A^\ominus$ denotes a colorless anion,
w denotes the valency of the anion A and
n denotes 0 or 1,
are obtained in a simple manner when a compound of the formula

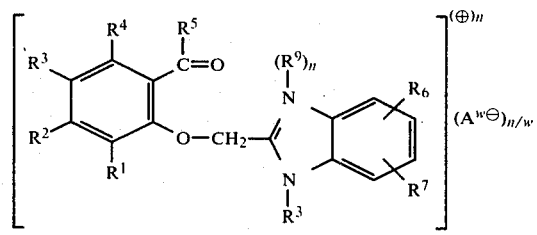

is heated to 110°–200° C. in an inert solvent, without the addition of a catalyst.

2 Claims, No Drawings

PROCESS FOR THE PREPARATION OF BENZIMIDAZOLYLBENZOFURANES

The invention relates to a process for the preparation of compounds of the formula

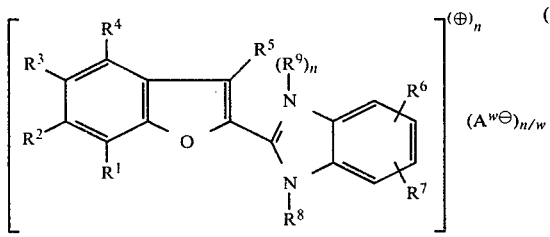

which is characterised in that a compound of the formula

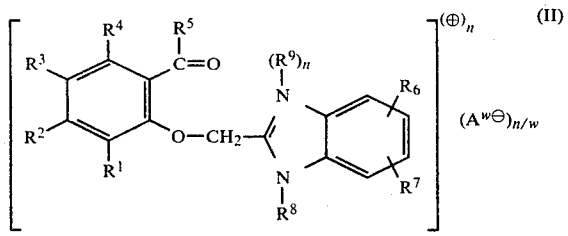

is heated in an inert organic solvent, without the addition of a catalyst.

In the general formulae (I) and (II):
$R^1$, $R^3$ and $R^4$ denote hydrogen, alkyl, alkoxy or halogen,
$R^2$ denotes hydrogen, halogen, alkyl, alkoxy, aryl or a substituent of the general formula

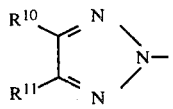

in which
$R^{10}$ denotes aryl, alkyl, aralkyl, styryl or alkoxy and
$R^{11}$ denotes hydrogen, CN, COOR, CONRR' or $R^{10}$, or two adjacent radicals from the group $R^1$, $R^2$, $R^3$, $R^4$, $R^{10}$ and $R^{11}$ together denote a fused-on hydroaromatic or aromatic ring,
$R^5$ denotes hydrogen, aryl or alkyl,
$R^6$ denotes hydrogen, halogen, alkyl, alkoxy, alkylsulphonyl, arylsulphonyl, CN, $CF_3$, COOR, $SO_3R$, CONRR' or $SO_2NRR'$,
$R^7$ denotes hydrogen, halogen, alkyl or alkoxy,
$R^8$ denotes hydrogen, alkyl, cycloalkyl, alkenyl, aryl or aralkyl,
$R^9$ denotes cycloalkyl, alkenyl, alkyl or aralkyl,
$A^\ominus$ denotes a colourless anion of an inorganic or organic acid,
w denotes the valency of the anion A,
n denotes 0 or 1,
R denotes alkyl and
R' denotes R or H,
and wherein the abovementioned hydrocarbon radicals and alkoxy radicals and the optionally fused-on ring systems can be substituted by substituents customary in brightener chemistry.

Any suitable alkyl and alkoxy radicals have 1–4 C atoms.

Suitable aryl radicals are phenyl radicals. Suitable non-ionic substituents are alkyl, alkoxy, halogen, CN, COOR, $SO_2R$ and many others. "Halogen" is understood, above all, as bromine and, in particular, chlorine.

Suitable alkenyl radicals have 3–5 C atoms.
Suitable cycloalkyl radicals are cyclohexyl radicals.
Suitable rings which $R^{10}$ and $R^{11}$ form are

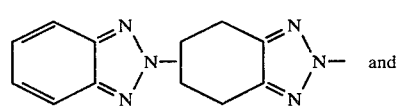

Suitable anions are halide, formate, acetate, lactate, alkyl-sulphate, aryl-sulphate, carbonate and bicarbonate.

It is to be described as exceptionally surprising that cyclisation is effected by simple heating, since catalysts, such as, for example, strong bases, usually have to be employed in the case of such cyclisation reactions (see, for example, DE-OS (German Published Specification) No. 2,238,628=U.S. Pat. No. 3,864,333).

The process according to the invention is appropriately carried out by a procedure in which a compound of the formula (II) is heated at temperatures of 80°–250° C., preferably at 110°–200° C., in an organic solvent until the splitting off of water has ended.

The new process proceeds particularly smoothly when the compounds of the formula (II) in which n=1 are used.

Suitable solvents for carrying out this reaction are all the solvents which are inert under the reaction conditions, especially aromatic hydrocarbons, such as benzene, toluene and xylene; halogenated hydrocarbons, such as trichloroethane, tetrachloroethylene, chlorobenzene, dichlorobenzene and trichlorobenzene, and furthermore nitrobenzene, alkanols and open-chain or cyclic ethers, such as butanol, dibutyl ether, diphenyl ether, ethylene glycol monomethyl ether, ethylene glycol monoethyl ether, anisole or dioxane; ketones, such as cyclohexanone or methyl ethyl ketone; fatty acid amides, such as dimethylformamide or dimethylacetamide; sulphoxides, such as dimethylsulphoxide; and carboxylic acid esters, such as ethyl acetate or butyl acetate. In this process, it is not necessary for the compounds of the formula (II) to dissolve in the solvents indicated; the cyclisation can also be carried out in suspension.

The compounds of the formula (II) are obtained, for example, by reacting a compound of the formula

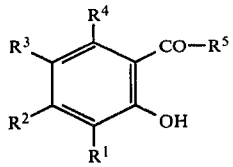

(III)

in which
R$^1$, R$^2$, R$^3$, R$^4$ and R$^5$ have the meaning indicated above,
with a compound of the formula

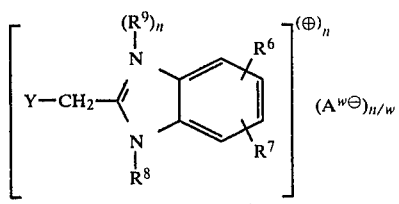

(IV)

in which
R$^6$, R$^7$, R$^8$ and R$^9$, A$^\ominus$, n and w have the meaning indicated above and
Y denotes chlorine or bromine,
in the presence of a weak base.

The appropriate procedure for this reaction is to react the compounds of the formulae (III) and (IV) in equimolar amounts in an organic solvent at 20°–120° C., preferably at 40°–90° C., in the presence of at least molar amounts of a base.

Examples of suitable solvents for carrying out this reaction are alcohols, such as methanol, ethanol or ethylene glycol monomethyl ether, ketones, such as, for example, acetone, methyl ethyl ketone or methyl isobutyl ketone, fatty acid amides, such as, for example, dimethylformamide or dimethylacetamide, sulphoxides, such as dimethylsulphoxide, and hexamethylphosphoric acid triamide.

Inorganic and organic bases, preferably alkali metal carbonates and bicarbonates and alkaline earth metal carbonates and bicarbonates, for example sodium carbonate and potassium carbonate, and tertiary amines, such as triethylamine or pyridine, can be used as the weak bases, which function as acid-binding agents.

If the compounds of the formula (III) are employed as alkali metal salts or alkaline earth metal salts, the addition of acid-binding agents can be dispensed with.

The compounds of the formula (III) are known, or they are readily accessible by processes which are known from the literature (see, for example, H. Giesecke and J. Hocker, Liebigs Annalen der Chemie, 1978, 345).

The compounds of the formula (IV) in which n=0 are prepared by the process described in U.S. Pat. No. 3,313,824, by reacting halogenoacetic acids with appropriately substituted o-phenylenediamines.

The compounds of the formula (IV) in which n=1 are obtained from the above products by quaternisation with a compound of the formula

R$^9$—A  (V)

in which
R$^9$ and A have the meaning indicated above.

A preferred process variant for the preparation of quaternary compounds of the formula (I) in which n=1 consists in first quaternising the corresponding compound of the formula (II) in which n=0 with a compound of the formula (V) in a suitable solvent and then cyclising the product, without intermediate isolation, at temperatures of 80°–250° C., preferably at 110°–200° C.

Dialkyl sulphates, such as dimethyl sulphate and diethyl sulphate, alkyl halides, such as methyl chloride, ethyl, propyl or butyl iodide or ethyl, propyl or butyl bromide, allyl chloride or bromide or crotyl chloride or bromide, and alkyl benzenesulphonates, such as p-methyl-, ethyl- or chlorobenzenesulphonate, are preferably used as the quaternising agents of the formula (V). If the preparation of compounds of the formula (I) which are quaternised with a benzyl radical is desired, benzyl halides, such as benzyl chloride, are preferably used for the benzylation. Examples of further quaternising agents are BrCH$_2$CH$_2$OH, BrCH$_2$CHOHCH$_3$, halogenoacetic acid derivatives, such as ClCH$_2$CO$_2$CH$_2$CH$_3$, BrCH$_2$COOH, BrCH$_2$COOCH$_3$, ClCH$_2$CN, ClCH$_2$CONH$_2$, ClCH$_2$CONHCH$_3$ and ClCH$_2$CON(CH$_3$)$_2$, and ethylene oxide or propylene oxide in the presence of suitable anions, such as, for example, anions of formic acid, acetic acid or lactic acid.

Suitable solvents for this one-pot process are in general all the inert solvents. Those which dissolve the starting material and from which the end product separates out immediately are preferred. Examples which may be mentioned are: aromatic hydrocarbons, such as benzene, toluene and xylene; halogenated hydrocarbons, such as trichloroethane, tetrachloroethylene, chlorobenzene or dichlorobenzene, and furthermore nitrobenzene, alkanols and open-chain or cyclic ethers, such as butanol, dibutyl ether, ethylene glycol monomethyl ether, ethylene glycol monoethyl ether, anisole or dioxane; ketones, such as cyclohexanone or methyl ethyl ketone; fatty acid amides, such as dimethylformamide or dimethylacetamide; sulphoxides, such as dimethylsulphoxide; and carboxylic acid esters, such as ethyl acetate or butyl acetate. In some cases it is advantageous to use excess alkylating agent as the solvent.

Some of the products prepared by the processes according to the invention are known valuable optical brighteners (compare DE-OS (German Published Specification) No. 2,031,774 and DE-OS (German Published Specification) No. 2,159,469).

Preferred process products correspond to the formula (I)
wherein
R$^1$, R$^3$ and R$^4$ hydrogen, methyl, ethyl, methoxy or chlorine,
R$^2$ hydrogen, chlorine, C$_1$–C$_4$-alkyl, C$_1$–C$_4$-alkoxy, phenyl which is substituted by C$_1$–C$_4$-alkyl and/or C$_1$–C$_4$-alkoxy or a substituent of the general formula

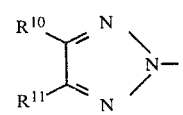

in which
R$^{10}$ C$_1$–C$_4$-alkyl, C$_1$–C$_4$-alkoxy, a phenyl radical, which can optionally be substituted by C$_1$–C$_4$-alkyl, phenyl, C$_1$–C$_4$-alkoxy or chlorine, benzyl or styryl.

$R^{11}$ hydrogen, cyano, carboxyl, $C_1$–$C_4$-alkylcarbonylamino, benzylamino or $R^{10}$, or $R^{10}$ and $R^{11}$ together a fused-on naphthalene or benzene ring, which can optionally be substituted by $C_1$–$C_4$-alkyl and/or $C_1$–$C_4$-alkoxy, $R^5$ hydrogen, alkyl with 1–4 C atoms, preferably methyl, or phenyl which is optionally substituted by methyl and/or methoxy, $R^6$ hydrogen, alkyl with 1–4 C atoms, preferably methyl, methoxy, chlorine, alkylsulphonyl with 1–4 C atoms, cyano, COOH, $SO_3H$, $COOR^8$, $SO_3R^8$ or $CON(R^5)_2$, $R^7$ hydrogen, methyl, methoxy or chlorine, $R^8$ alkyl with 1–4 C atoms, preferably methyl, hydroxyalkyl with 2–4 hydrocarbon atoms, cyanoethyl, phenyl which is optionally substituted by chlorine, methyl or methoxy, cyclohexyl or benzyl, $R^9$ alkyl with 1–4 C atoms which is optionally substituted by hydroxyl or alkyl with 1–4 C atoms, and preferably methyl, benzyl which is optionally substituted by chlorine or methoxy, a radical —$CH_2$—CN, —$CH_2$—$CONH_2$ or —$CH_2$—$COOR^8$ or cylohexyl, $A^-$ halide, formate, acetate, lactate, $CH_3SO_4^-$, $C_2H_5SO_4^-$, $C_6H_5SO_3^-$, p—$CH_3$—$C_6H_4$—$SO_3^-$, p—Cl—$C_6H_4$—$SO_3$, carbonate or bicarbonate, w the valency of the anion A and n represents 0 or 1.

EXAMPLE 1

10 g of the compound of the formula

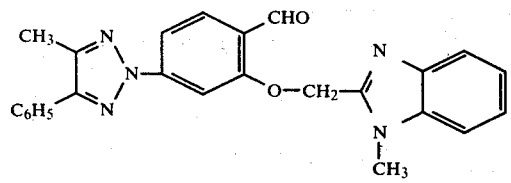

are stirred in 100 ml of 1,2-dichlorobenzene at 170° C. for 7 hours, during which the water formed is distilled off. The mixture is then cooled with an ice-bath and filtered and the filter cake is washed with 20 ml of methanol. After drying, 8.5 g (89% of theory) of the compound of the formula

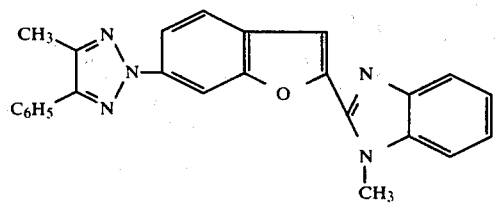

of melting point 222°–4° C. are obtained.

The compound of the formula (VI) is obtained by the following route:

14.0 g of 4-(4-methyl-5-phenyl-1,2,3-triazol-2-yl)-salicylaldehyde, 9.9 g of 2-chloromethyl-1-methylbenzimidazole and 6.4 g of anhydrous sodium carbonate are stirred in 100 ml of dimethylformamide at 70° C. for 5 hours. 100 ml of water are then added and the solid is filtered off at room temperature and rinsed with 100 ml of water. It is dried at 100° C. and 20.7 g (98% of theory) of the compound of the formula (VI) of melting point 216°–18° C. are thus obtained. When recrystallised from methylglycol, the product melts at 236° C.

EXAMPLE 2

10 g of the compound of the formula (VI) ar dissolved in 90 ml of 1,2-dichlorobenzene at 140° C. and a solution of 3.4 g of dimethyl sulphate (97% pure) in 10 ml of I,2 dichlorobenzene is added dropwise in the course of 10 minutes. The mixture is then stirred at 140° C. for 4 hours and the water formed is distilled off continuously. The mixture is allowed to cool to 80° C. and the solid is filtered off and washed with 20 ml of acetone. After drying at 100° C., 11.6 g (93% of theory) of the compound of the formula

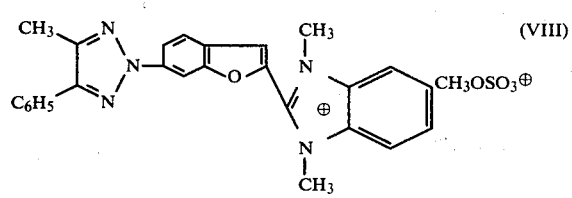

of melting point 260°–1° C., are obtained.

If diethyl sulphate is used instead of dimethyl sulphate and the procedure is otherwise as described above, the compound of the formula

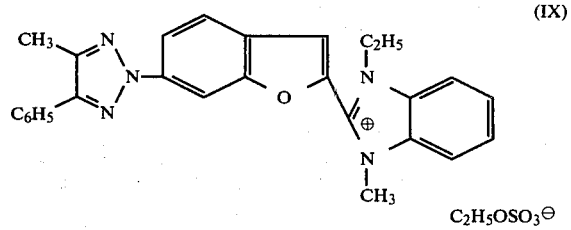

is obtained.

Melting point: 195°–7° C.

Yield: 91% of theory.

EXAMPLE 3

Using the phenol ethers of the formulae

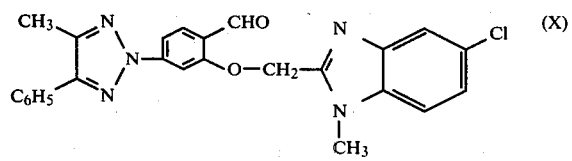

Melting point: 205°–6° C.

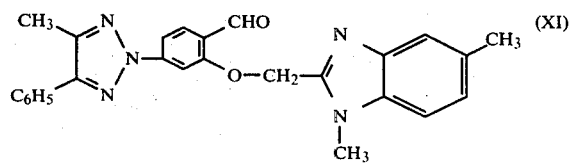

Melting point: 197°–8° C.

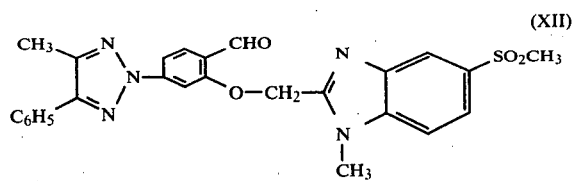
(XII)
Melting point: 255°-6° C.
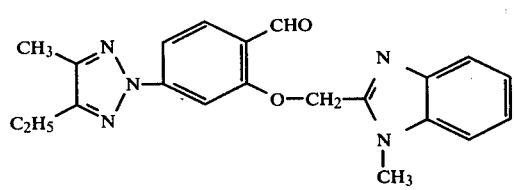
(XIII)
Melting point: 195° C.
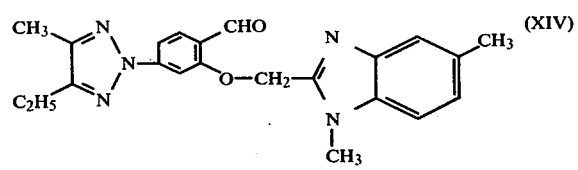
(XIV)
Melting point: 192°-3° C.
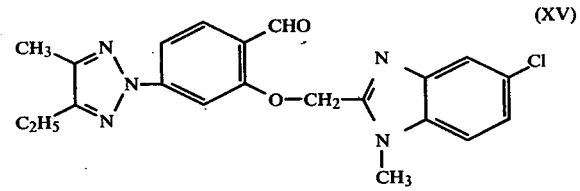
(XV)
Melting point: 208°-9° C.
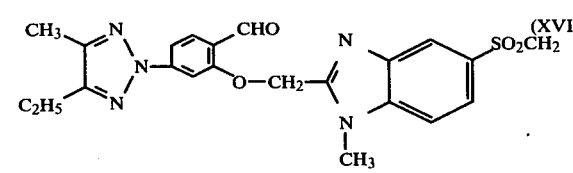
(XVI)
Melting point: 212°-3° C.
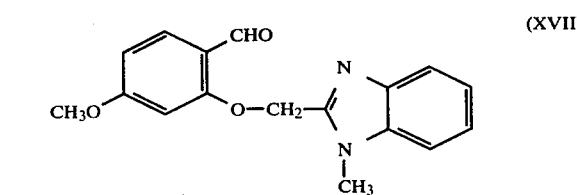
(XVII)
Melting point: 138°-40° C.
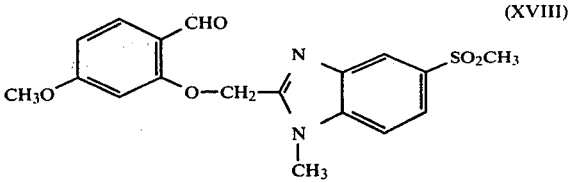
(XVIII)
Melting point: 209°-10° C.
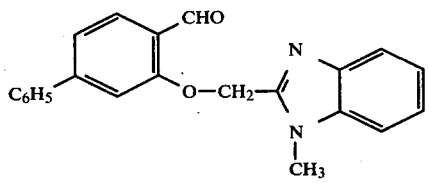
(XIX)
Melting point: 178° C.
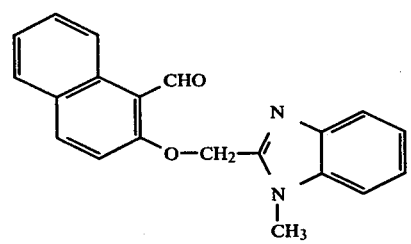
(XX)
Melting point: 217°-8° C.
The following compounds are obtained analogously to Example 1:
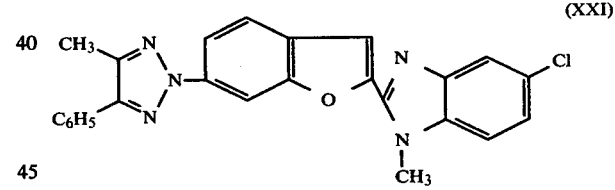
(XXI)
Melting point: 230°-1° C.
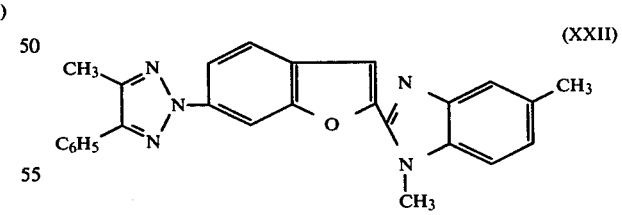
(XXII)
Melting point: 220° C.
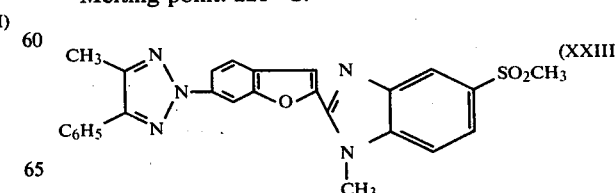
(XXIII)
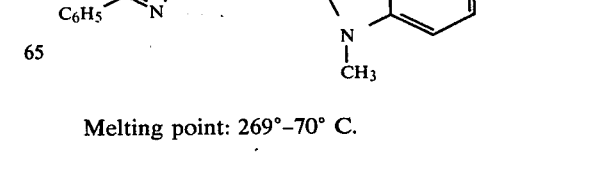
Melting point: 269°-70° C.

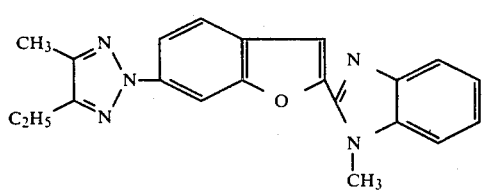 (XXIV)

Melting point: 180° C.

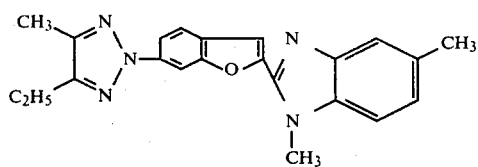 (XXV)

Melting point: 214°–15° C.

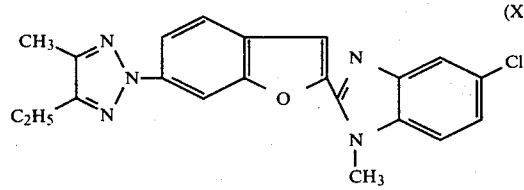 (XXVI)

Melting point: 196° C.

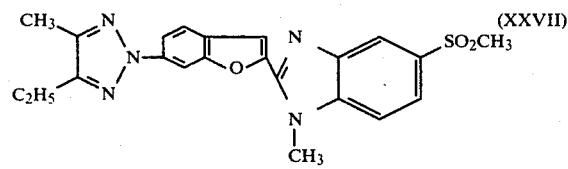 (XXVII)

Melting point: 224°–6° C.

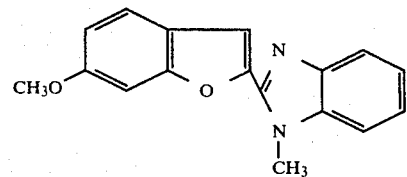 (XXVIII)

Melting point: 251° C.

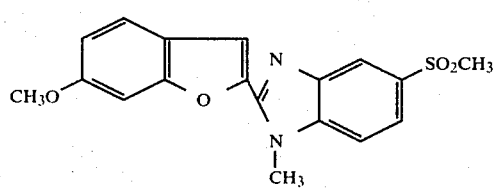 (XXIX)

Melting point: 205° C.

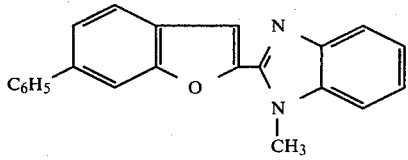 (XXX)

Melting point: 218° C.

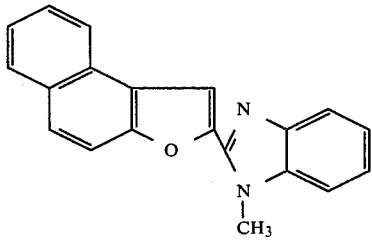 (XXXI)

Melting point: 212° C.

The preparation of the compounds of the formulae (X–XX) is effected analogously to the synthesis of the compound of the formula (VI) (compare Example 1), from the appropriately substituted salicylaldehydes and 2-chloromethyl-1-methylbenzimidazoles.

EXAMPLE 4

If the compound of the formula (VI) is replaced by the compounds of the formulae (X–XX) and the procedure followed is otherwise as described in Example 2, the quaternary compounds of the following formulae are obtained

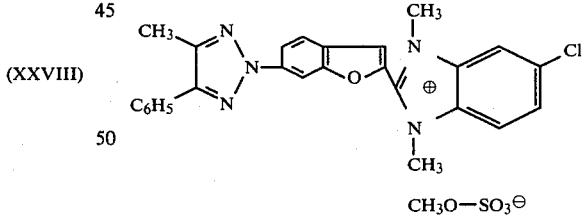 (XXXII)

Melting point: 240° C. (decomposition).

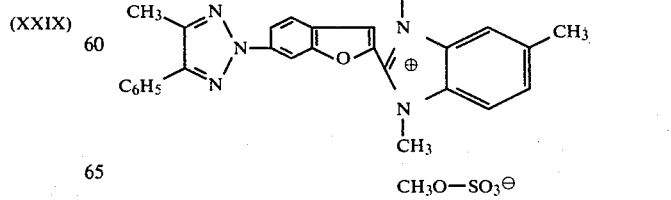 (XXXIII)

Melting point: 230° C. (decomposition).

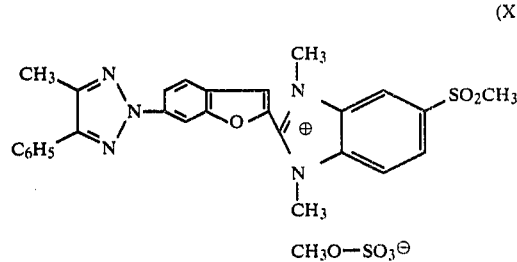

Melting point: 273°-5° C.

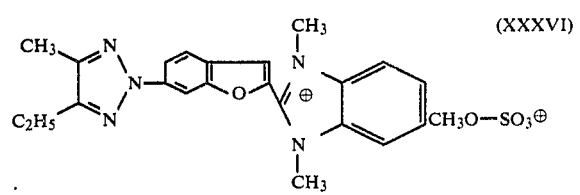

Melting point: 240°-5° C.

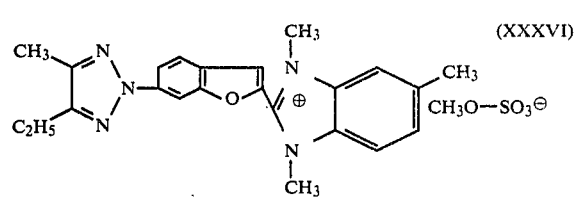

Melting point: 235°-8° C.

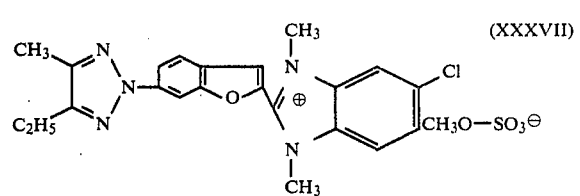

Melting point: 210° C.

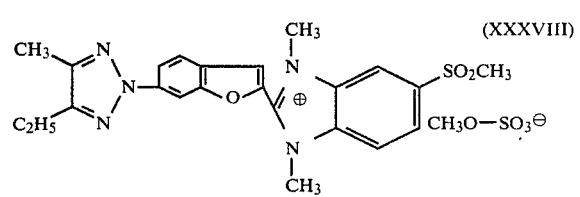

Melting point: 263°-8° C.

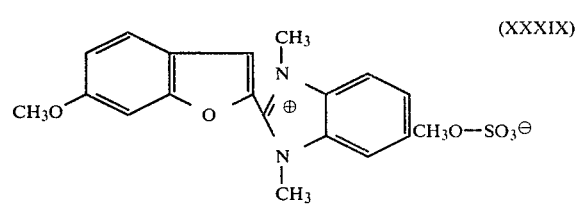

Melting point: 224°-5° C.

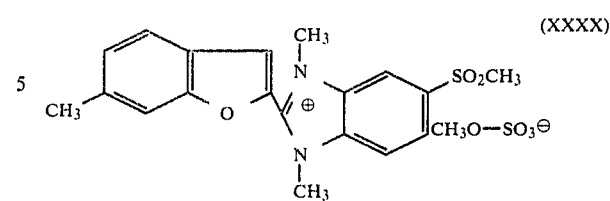

Melting point: 194°-7° C.

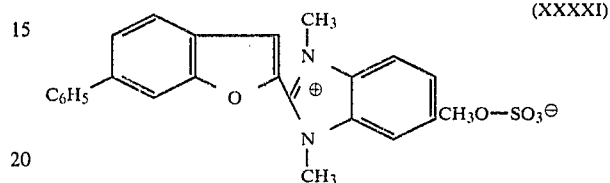

Melting point: 203°-6° C.

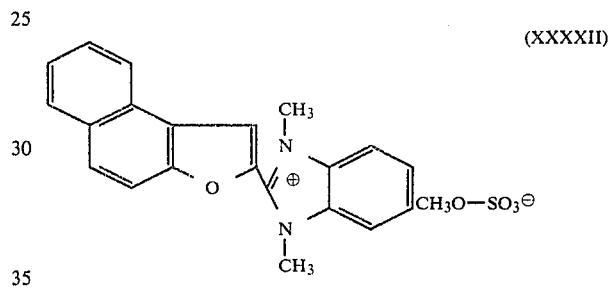

Melting point: 202°-4° C.

EXAMPLE 5

If the compound of the formula (VI) is replaced by the compounds of the formulae

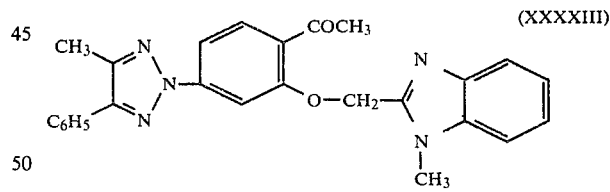

Melting point: 243° C.

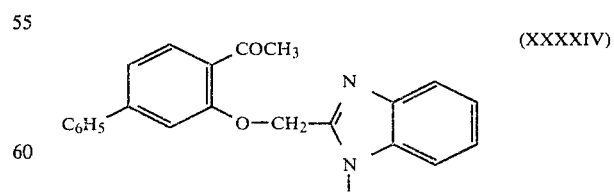

Melting point: 168°-71° C.

and the procedure followed is otherwise as described in Example 1, the benzimidazolylbenzofuranes of the following formulae are obtained

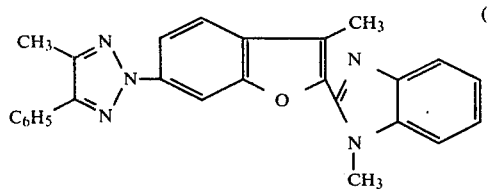

(XXXXV)

Melting point: 215°-6° C.

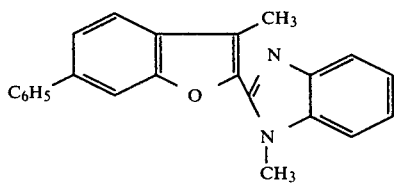

(XXXXVI)

Melting point: 165°-8° C.

EXAMPLE 6

Using the phenol ethers (XXXXIII) and (XXXXIV), the following quaternary compounds are obtained analogously to Example 2:

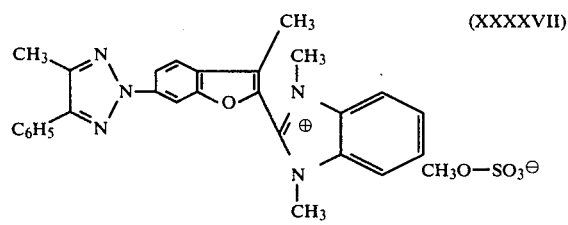

(XXXXVII)

Melting point: 291° C.

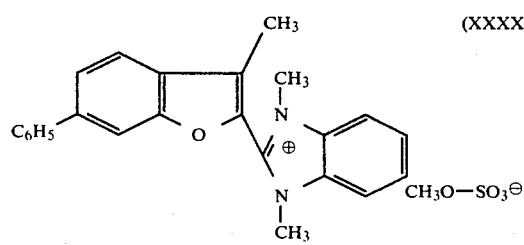

(XXXXVIII)

Melting point: 151°-2° C.

We claim:

1. In the preparation of a compound of the formula

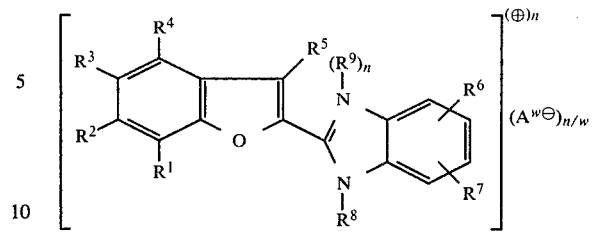

wherein
$R^1$, $R^3$ and $R^4$ each independently is hydrogen, alkyl, alkoxy or halogen,
$R^2$ is hydrogen, halogen, alkyl, alkoxy, aryl or a substituent of the formula

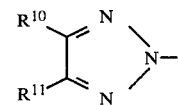

$R^{10}$ is aryl, alkyl, aralkyl, styryl or alkoxy and
$R^{11}$ is hydrogen, CN, COOR, CONRR' or $R^{10}$, or two adjacent radicals from the group $R^1$, $R^2$, $R^3$, $R^4$, $R^{10}$ and $R^{11}$ together form a fused-on hydroaromatic or aromatic ring,
$R^5$ is hydrogen, aryl or alkyl,
$R^6$ is hydrogen, halogen, alkyl, alkoxy, alkylsulphonyl, arylsulphonyl, CN, $CF_3$, COOR, $SO_3R$, CONRR' or $SO_2NRR'$,
$R^7$ is hydrogen, halogen, alkyl or alkoxy,
$R^8$ is hydrogen, alkyl, cycloalkyl, alkenyl, aryl or aralkyl,
$R^9$ is cycloalkyl, alkenyl, alkyl or aralkyl,
$A^\ominus$ is a colorless anion of an inorganic or organic acid,
w is the valence of the anion A,
n is 0 or 1,
R is alkyl, and
R' is R or hydrogen,
and wherein the above-mentioned hydrocarbon radicals and alkoxy radicals and the optionally fused-on ring systems can be substituted by substituents customary in brightener chemistry, by heating a compound of the formula

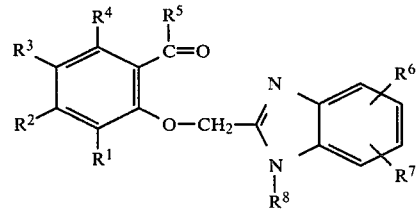

in the presence of a quaternizing agent containing an $R^9$ radical, the improvement which comprises effecting the heating in an inert solvent without the addition of a catalyst.

2. A process according to claim 1, wherein the reaction is carried out at 110°-200° C. until the splitting off of water has ended.

* * * * *